United States Patent [19]

Pielartzik et al.

[11] Patent Number: 5,143,956
[45] Date of Patent: * Sep. 1, 1992

[54] FREE-FLOWING POLYAMIDE MOLDING COMPOUNDS

[75] Inventors: Harald Pielartzik; Hans-Detlef Heinz; Rolf Dhein, all of Krefeld; Aziz E. Sayed, Leverkusen, all of Fed. Rep. of Germany

[73] Assignee: Bayer Aktiengesellschaft, Leverkusen, Fed. Rep. of Germany

[ * ] Notice: The portion of the term of this patent subsequent to Apr. 7, 2009 has been disclaimed.

[21] Appl. No.: 656,680

[22] Filed: Feb. 19, 1991

[30] Foreign Application Priority Data

Mar. 1, 1990 [DE] Fed. Rep. of Germany ....... 4006404

[51] Int. Cl.$^5$ .......................... C08K 5/20; C08K 5/17; C08K 5/10
[52] U.S. Cl. .................................. 524/219; 524/237; 524/291; 524/293; 524/299
[58] Field of Search ............... 524/219, 237, 291, 293, 524/299, 451

[56] References Cited

U.S. PATENT DOCUMENTS 3,962,314 6/1976 Economy et al. ................... 260/473
4,611,025 9/1986 Akkapeddi et al. ................ 524/451

FOREIGN PATENT DOCUMENTS 0359037 3/1990 European Pat. Off. .
5082150 6/1991 Japan .................................. 524/293

Primary Examiner—Paul R. Michl
Assistant Examiner—Peter Szekely
Attorney, Agent, or Firm—Connolly and Hutz

[57] ABSTRACT

The invention relates to free-flowing polyamide molding compounds which are characterized by a content of new liquid-crystalline compounds corresponding to general formulae (I) and/or (II) and to the new liquid-crystalline compounds corresponding to general formulae (I) and/or (II).

16 Claims, No Drawings

FREE-FLOWING POLYAMIDE MOLDING COMPOUNDS

This invention relates to new, free-flowing polyamide molding compounds which are characterized by a content of new liquid-crystalline compounds corresponding to general formulae (I) and/or (II) and to the new liquid-crystalline compounds corresponding to formulae (I) and/or (II).

Polyamides are a class of polymers which have been successfully used for several years for a number of practical applications. They may be produced by various processes and may be synthesized from various polyamide-forming components. For special applications, they may be processed either individually or even in combination with processing aids, polymeric blending components or even mineral reinforcing materials (for example fillers or glass fibers) to form materials having special combinations of properties. Thus, polyamides are industrially used in large quantities for the production of fibers, moldings and films and also, for example, as hotmelt adhesives and auxiliaries in a variety of applications.

A very large percentage of the various polyamide molding compounds is processed by injection molding, i.e. the polyamide is melted and introduced under pressure into a mold in which it solidifies on cooling. Flowability plays a key role in this regard. The more easily a polyamide melt flows, the better the mold can be filled. This is of paramount importance above all in the case of very thin-walled moldings.

Whereas partially crystalline polyamides of average molecular weight show good flow properties, these good flow properties deteriorate rapidly on account of the considerable increase in melt viscosity with increasing molecular weight during the transition to relatively high molecular weight polyamides. In view of the fact that the mechanical properties of polyamides, particularly their impact strength, become even better with increasing molecular weight, this deterioration in flowability seriously restricts their potential applications.

In contrast to partially crystalline aliphatic polyamides, amorphous polyamides show very high melt viscosities and correspondingly poor flow, even for relatively low molecular weights, particularly when their glass temperatures are above about 150° C. Accordingly, they are difficult to process in this case, too.

It is known that partially crystalline polyamides take up different quantities of water, depending on their structure. This leads to an increase in toughness but to a reduction in rigidity because the water acts as a plasticizer.

Accordingly, inorganic reinforcing materials, for example glass fibers or mineral fillers, have long been incorporated in polyamides to increase their rigidity.

However, the increase in rigidity, hardness, heat resistance and dimensional stability achieved with inorganic reinforcing materials is generally offset by disadvantages, particularly a reduction in flow, above all in the case of fibrous reinforcing materials, which makes the polyamides difficult to process.

The effect of the reduction in flow is that more and more injection points are required to fill the mold, particularly in the case of moldings of large surface area, in other words the molds become increasingly more expensive. As a result, there is also an increase in the number of unwanted weld lines which can impair the appearance and mechanical performance properties of the moldings. In addition, it becomes very difficult to produce satisfactory surface qualities and thin-walled moldings.

Accordingly, it would be of considerable technological significance if the flowability of the above-mentioned polyamides could be drastically improved.

Polyamide blends show different properties from pure polyamides, depending on the type of polymeric blending component, and are therefore particularly valuable materials.

High-impact polyamides, for example, are well-known blends. High-impact polyamides are two-phase polymer blends which contain special elastomeric components to increase the impact strength or notched impact strength of polyamides in the freshly molded state or even at low temperatures. Examples of such blending components are, for example, diene and acrylate rubbers, EPDM, ethylene/acrylic acid copolymers and others of the type described in large numbers in the prior art.

Reinforcing materials may be present in addition to the elastomer modifier. In blends such as these, therefore, both toughness and rigidity are increased in relation to unmodified polyamides.

Another large group of polyamide blends contains, for example, amorphous thermoplastics which show an increased glass temperature and rigidity in relation to standard polyamides.

This reduces the water uptake of the polyamides and increases their heat resistance (as measured for example by the heat distortion temperature (HDT)) and rigidity. Examples of blending components of this type are polystyrene, ABS, polycarbonate, aromatic polyester (carbonates), polyphenylene oxides, polymethyl methacrylate, polyether sulfones, etc. These blends may also contain impact modifiers.

Blends of polyamides with partially crystalline thermoplastics are also known.

However, the disadvantage is that these polyamide blends also generally show greatly reduced flow in relation to the pure polyamide component which makes them difficult to process. This applies in particular where the blends additionally contain reinforcing materials.

Accordingly, it would also be of considerable technological importance to these materials if their flowability could be distinctly increased to make them easier to process into high-quality moldings. The processing temperature could also be reduced in this way, imposing less strain on the material. This would have a positive effect above all on blends containing rubber modifiers.

It has now surprisingly been found that special liquid-crystalline, low molecular weight and/or oligomeric additives (I and/or II) produce a drastic increase in the flowability of polyamide molding compounds, even when added to the polyamides in very small quantities. In addition, a number of mechanical properties and, in some cases, heat resistance can also be improved by this measure. In addition, the water uptake of the polyamides, their crystallization rate and their degree of crystallization may also be increased by this measure, resulting in improved dimensional stability of moldings and longer processability of opened containers and, in some cases, shorter cycle times.

Accordingly, the present invention relates to new, free-flowing polyamide molding compounds, characterized in that they are prepared by mixing of
1) 85 to 99.9% by weight polyamides known per se with
2) 0.1 to 15% by weight, preferably 0.3 to 8% by weight and more preferably 0.5 to 5% by weight low molecular weight, liquid-crystalline hydroxyl groups containing esters and/or ester amides ("LC flow promoters") corresponding to general formula (I)

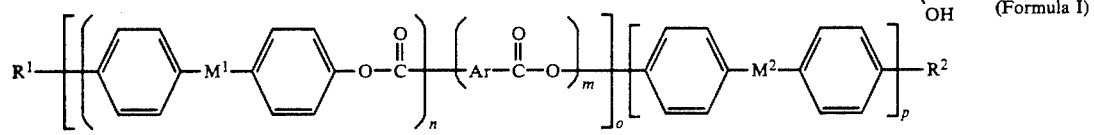

in which

—Ar is a $C_{6-20}$ aromatic radical which may be mononuclear or polynuclear; the polynuclear radical may be attached by a bond or may be fused, $R^1$ and $R^2$ may be the same or different and at least one of the substituents $R^1$ and $R^2$ is a group of the formula (III)-(XI) and the second of the substituents $R^1$ and $R^2$ may correspond to a hydroxyl-free group:

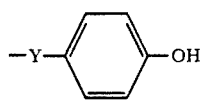 (III)

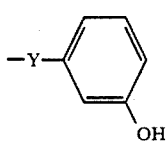 (IV)

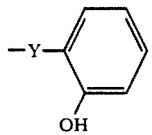 (V)

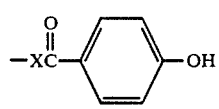 (VI)

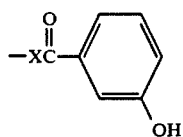 (VII)

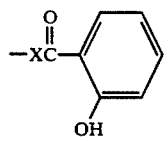 (VIII)

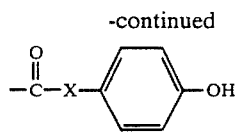 (IX)

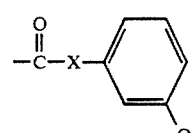 (X)

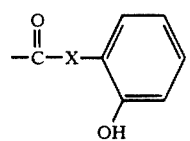 (XI)

Y is a chemical bond or a difunctional $C_{1-10}$ hydrocarbon radical or even an —$SO_2$ group, preferably a chemical bond or a —$C(CH_3)_2$ group, X is O or NH;

the aromatic rings in formulae (III)-(XI) may even be substituted, for example by halogen atoms or alkyl groups, —$M^1$ and —$M^2$ may be the same or different and represent radicals with two bonds corresponding to formulae I.1) to I.11)

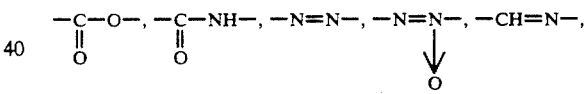

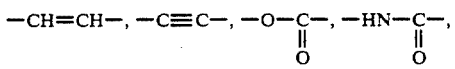

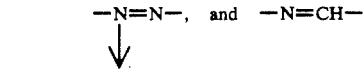

(formulae (I.1)–(I.11) corresponding to their sequence),
m = 0, 1 or 2,
n = 1 or 2,
o = 1, 2, 3 or 4 and
p = 0 or 1,
and/or liquid-crystalline oligomeric esters and/or ester amides corresponding to formula (II) with statistical distribution of the structural units (Formula II)

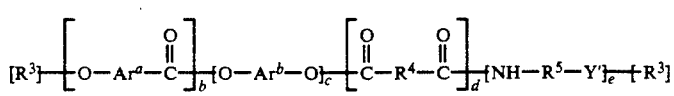

in which (Formula II)

$Ar^a$ is a difunctional, optionally substituted (substituents as in $R^3$) mononuclear or polynuclear aromatic radical containing 6 to 24 carbon atoms; the polynuclear radical may be directly attached or even fused and the carboxyl group may even be attached to the aromatic ring by an aliphatic radical, $Ar^b$ is a difunctional, optionally substituted, mononuclear or polynuclear aromatic radical containing 6 to 30 carbon atoms; the polynuclear radical may be attached in different ways $R^4$ and $R^5$ represent an alkyl radical containing 0 to 40 ($R^4$) or 3 to 40 ($R^5$) carbon atoms or both $R^4$ and $R^5$ may represent a cycloaliphatic radical containing 5 to 15 carbon atoms or have the meaning of an optionally substituted, difunctional, mononuclear or polynuclear aromatic radical containing 6 to 24 carbon atoms; the polynuclear radical may be attached differently by a bond or even by fusion, Y' represents —O—,

or —NH—, b=0 to 10, 0 to 8 and more preferably 0 to 4,
c=1 to 9, preferably 1 to 7, more preferably 1 to 4,
d=0 to 9, preferably 0 to 7 and more preferably 0 to 3,
e=0 to 3 and preferably 0 to 2
and in which $R_3$, depending on its attachment to the other units, represents substituents corresponding to formulae (XII)-(XIV)

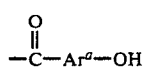 (XII)

 (XIII)

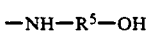 (XIV)

where the symbols are as already defined, the average molecular weight $\overline{M}n$ of the compounds corresponding to formula (II) being no greater than 4000 and preferably no greater than 2500, and, optionally, 3) from 0.001 to 150% by weight, based on the total weight of components 1) and 2), of standard additives; the additives may even completely or partly be present in the polyamides mentioned under 1).

The two substituents $R^1$ and $R^2$ are preferably of the type bearing hydroxyl (phenol) groups (III)-(XI).

Compounds Corresponding to Formula (I):

Particularly preferred groups —Ar— of formula (I) and groups $Ar^a$ and $Ar^b$ are the groups (Ar1) to (Ar4)

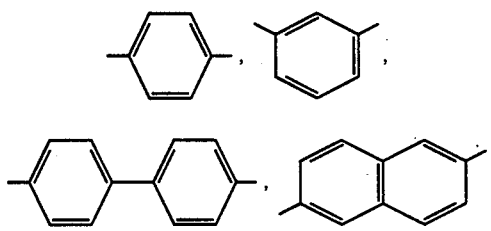

(Ar1)-(Ar4) in accordance with their sequence.

Preferred substituents $R^1$ and $R^2$ are the groups (III), (IV) and (IX).

Preferred groups —M— are those corresponding to formulae (I.1), (I.2), (I.5), (I.8), (I.9) and (I.11).

Preferred index combinations m, n, o, p and q are m=0, n=1, o=1, p=0;
m=0, n=1, o=1, p=1;
m=0, n=2, o=1, p=1;
m=n=o=p=1;
m=1, n=1, o=2, p=1;
m=0, n=2, o=1, p=0;
m=1, n=2, o=1, p=1 and
m=1, n=1, o=3, p=1.

The compounds corresponding to formula (I) are distinguished by the fact that, on melting, they pass through a liquid crystalline phase. (For liquid crystalline compounds and phases, see for example D. Demus, L. Richter, Textures of Liquid Crystals, Verlag Chemie, Weinheim—New York, 1978, or H. Kelker, R. Hatz, Handbook of Liquid Crystals, Verlag Chemie, Weinheim, Deerfield 1980).

Preferred compounds of formula (I) are those which contain 3 to 25 aromatic partial structures, the group —Ar— being selected as a partial structure irrespective of whether it is mononulcear or polynuclear. Particularly preferred compounds of formula (I) are those which contain 4 to 15 aromatic partial structures, the group —Ar— again being selected as an aromatic partial structure irrespective of whether it is mononuclear or polynuclear. Especially preferred compounds of formula (I) are those which contain 4 to 10 aromatic partial structures as defined above.

The following four groups of compounds (I,A) to (I,D) are mentioned as examples of compounds corresponding to formula (I):

(I,A) liquid crystalline compounds corresponding to formula (I) containing three aromatic partial structures, in which m=0, n=1, o=1 and p=0,

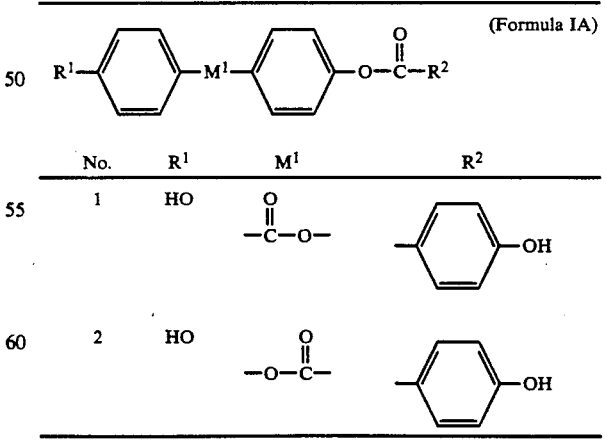

(I,B) liquid crystalline compounds corresponding to formula (I) containing four aromatic partial structures, in which again m=0, n=1, o=1 and p=0:

(Formula IB)

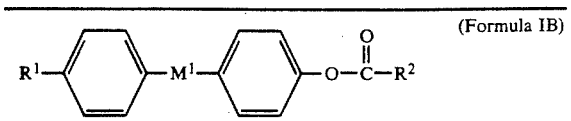

| No. | R¹ | M¹ | R² |
|---|---|---|---|
| 3 | HO–⌬–C(O)–O– | –C(O)–O– | –⌬–OH |
| 4 | HO–⌬–C(O)–O– | –O–C(O)– | –⌬–OH |

-continued (Formula IB)

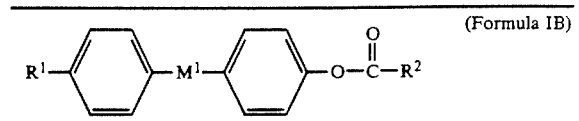

| No. | R¹ | M¹ | R² |
|---|---|---|---|
| 5 | HO–⌬–O–C(O)– | –C(O)–O– | –⌬–OH |

(I,C) liquid crystalline compounds corresponding to formula (I) containing five aromatic partial structures, in which m=n=o=p=1.

(Formula IC)

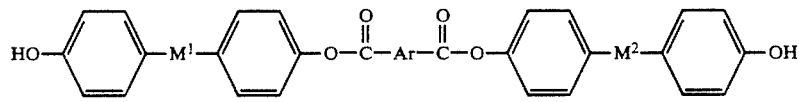

| No. | M¹ | M² | Ar |
|---|---|---|---|
| 6 | –O–C(O)– | –C(O)–O– | ⌬ |
| 7 | " | " | ⌬–⌬ |
| 8 | –C(O)–O– | –O–C(O)– | ⌬ |
| 9 | " | " | ⌬–⌬ |

(I,D) liquid crystalline compounds corresponding to formula (I) containing seven aromatic partial structures, in which m=n=o=p=1:

(formula ID)

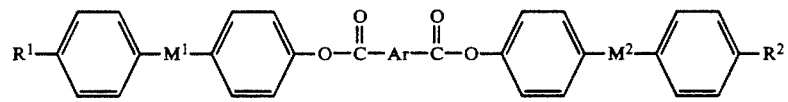

| No. | R¹ | M¹ | Ar | M² | R² |
|---|---|---|---|---|---|
| 10 | HO–⌬–C(O)–O– | –C(O)–O– | ⌬ | –O–C(O)– | –O–C(O)–⌬–OH |
| 11 | HO–⌬(m)–C(O)–O– | –C(O)–O– | ⌬ | –O–C(O)– | –O–C(O)–⌬(m)–OH |

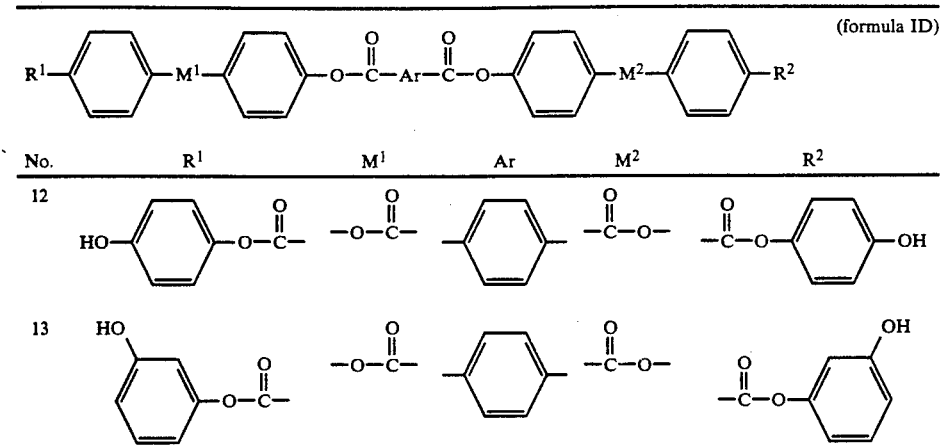

The low molecular weight, liquid crystalline additives (I) which may be used in accordance with the invention may be produced—optionally using protective groups—analogously to the compounds of applicants' own hitherto unpublished patent application. A characteristic method for their production is described in the Examples.

The low molecular weight, liquid crystalline additives corresponding to formula (I) are preferably used in quantities of 0.3 to 8% by weight and more preferably in quantities of 0.5 to 5% by weight either individually or in admixture.

Compounds Corresponding to Formula (II)

Suitable difunctional aromatic radicals ($Ar^a$) in formula (II) are those based on aromatic hydroxycarboxylic acids corresponding to the following formulae

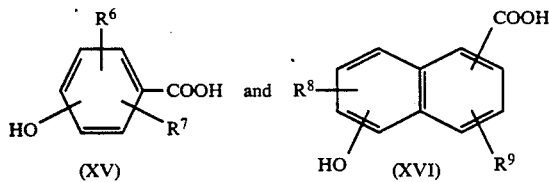

in which $R^6$ to $R^9$ represent $C_{1-4}$ alkyl (preferably methyl, ethyl), $C_{1-4}$ alkoxy (preferably methoxy, ethoxy), $C_{6-10}$ aryl or aryloxy (preferably phenyl, phenyloxy, naphthyl, naphthyloxy, biphenyl, biphenyloxy, tolyl, tolyloxy), $C_{7-12}$ alkylaryl (preferably benzyl), halogen (preferably chlorine and bromine) or hydrogen and the valencies between nucleus and hydroxyl group and between nucleus and carboxyl group form an angle of 45° to 180°.

In exceptional cases, the carboxyl groups of the compounds corresponding to formulae (XV) and (XVI) may even be attached to the aromatic radicals by alkylene groups.

Preferred aromatic hydroxy carboxylic acids are 4-hydroxy-3-methyl benzoic acid, 4-hydroxy-3-methoxy benzoic acid, 4-hydroxybenzoic acid, 3-hydroxybenzoic acid, 6-hydroxy-2-naphthoic acid. 4-Hydroxybenzoic acid, 3-hydroxy benzoic acid and 6-hydroxy-2-naphthoic acid are particularly preferred.

The aromatic hydroxy carboxylic acids have the OH group preferably symmetrical (1,4-phenylene or 2,6-naphthylene or 4,4'-diphenyl positions) to the carboxyl group.

Suitable difunctional aromatic radicals ($Ar^b$) corresponding to formula (II) are those based on diphenols corresponding to formula (IX)

$$HO-Z-OH \qquad (IX)$$

in which

Z is a difunctional, mononuclear or polynuclear aromatic radical containing 6 to 30 carbon atoms, the structure of Z being such that the two OH groups are each directly attached to a carbon atom of an aromatic system and the two valencies form an angle of 45° to 180°.

The aromatic radicals may be substituted by 1 to 4 $C_{1-4}$ alkyl, $C_{1-4}$ alkoxy, phenyl, phenoxy, benzyl groups or halogen atoms (preferably chlorine and bromine) and, in addition to m-/p-phenylene, 2,6- and/or 1,5-naphthylene and 4,4'-biphenylene radicals, also include phenylene radicals attached by oxygen, sulfur, carbonyl, sulfonyl or azomethine, $C_{1-18}$ and preferably $C_{1-4}$ alkylene or alkylidene, (alkyl-substituted) cyclohexylene or hexylidene or —$O(CH_2)_nO$— with n=2 to 4.

Preferred diphenols are, for example, hydroquinone, 4,4'-dihydroxydiphenyl, 4,4'-dihydroxydiphenyl ether, 4,4'-dihydroxydiphenyl ethane, 4,4'-dihydroxydiphenoxy ethane, 3,5'-dihydroxydiphenyl, 3,5'-dihydroxydiphenyl ether, 1,5-dihydroxynaphthalene, 2,6-dihydroxynaphthalene, 1,4-dihydroxynaphthalene, methyl hydroquinone, phenyl hydroquinone, 2,2'-dimethyl-4,4'-dihydroxydiphenyl, 3,3',5,5'-tetramethyl-4,4'-dihydroxydiphenyl,1,2-(2-chloro-4-hydroxyphenoxy)-ethane, 4-methoxy-2,6-dihydroxy naphthalene, resorcinol, 3,4'-dihydroxydiphenyl, 1,6-dihydroxy naphthalene, 1,7-dihydroxy naphthalene, 2,7-dihydroxy naphthalene, 4-chlororesorcinol, 4-phenyl resorcinol, 4-ethoxy resorcinol, 2,5-dichloro-1,6-dihydroxy naphthalene and 4-methoxy-2,7-dihydroxy naphthalene.

Particularly preferred diphenols are hydroquinone and 4,4'-dihydroxydiphenyl.

Suitable difunctional radicals ($R^4$) corresponding to formula (II) are those based on dicarboxylic acids corresponding to formula (X)

$$HOOC-R^4-COOH \qquad (X)$$

in which $R^4$ represents $C_mH_{2m}$ with m=0–40, preferably 0–20 and 30–38 or even a cycloaliphatic radical containing 5 to 15 carbon atoms or, preferably, a difunctional aromatic radical containing 6 to 24 carbon atoms and preferably 6 to 16 carbon atoms, the two valencies forming an angle of 45° to 180°. The difunctional aromatic radicals may be substituted by 1 to 4 $C_{1-4}$ alkyl, $C_{1-4}$ alkoxy, phenyl, phenoxy, benzyl groups or halogen atoms (preferably chlorine and bromine) and, in addition to 1,4-phenylene groups, 1,5- or 2,6-naphthylene groups and 4,4'- or 3,5'-biphenylene groups, also include phenylene groups attached by oxygen, sulfur, carbonyl, sulfonyl, $C_{1-4}$ alkylene or alkylidene, cyclohexylene or hexylidene or —O(CH$_2$)$_n$O— with n=1 to 4, preferably in symmetrical substitution ("para-position").

The following (cyclo)aliphatic dicarboxylic acids are preferred: oxalic acid, succinic acid, adipic acid, suberic acid, azelaic acid, trimethyl adipic acid, sebacic acid, dodecanedioic acid, dimer fatty acids and 1,4-cyclohexane dicarboxylic acid.

Oxalic acid, adipic acid, sebacic acid and dimer fatty acids are particularly preferred.

Preferred aromatic dicarboxylic acids are those based on the following difunctional groups: 1,4-phenylene, 1,4-naphthylene or 4,4'-biphenylene, in which the two bonds extend coaxially in opposite directions, or 1,5-naphthylene groups, 2,6-naphthylene groups or 3,5'-biphenylene groups, in which the two bonds extending in opposite directions are displaced parallel to one another, and 1,3-phenylene groups, 1,3-, 1,6-, 1,7- or 2,7-naphthylene groups or 3,4'-biphenylene groups in which the two bonds are not situated at adjacent atoms and do not extend in opposite directions either coaxially or displaced parallel to one another.

Preferred aromatic dicarboxylic acids are 1,4-naphthalene dicarboxylic acid, 1,5-naphthalene dicarboxylic acid, 2,6-naphthalene dicarboxylic acid, biphenyl-4,4'-dicarboxylic acid, biphenyl-3,3'-dicarboxylic acid, diphenoxyethane-4,4'-dicarboxylic acid, diphenyl ether-4,4'-dicarboxylic acid, methyl terephthalic acid, methoxyterephthalic acid, chloroterephthalic acid, 4-chloronapthalene-2,7-dicarboxylic acid, 2,6- or 2,7-naphthalene dicarboxylic acid, biphenyl-3,4'-dicarboxylic acid, 4-methyl isophthalic acid, 5-methyl isophthalic acid, diphenylether-4,4'-dichloro-3,3'-dicarboxylic acid, isophthalic and terephthalic acid.

Isophthalic and terephthalic acid are particularly preferred.

It is possible to use aliphatic or aromatic dicarboxylic acids both alone and in the form of mixtures.

Suitable difunctional groups ($R^5$) of formula (II) are those based on amino compounds corresponding to formula (XI)

$$H_2N-R^5-Y \quad (XI)$$

in which $R^5$ represents $C_mH_{2m}$ with m=3 to 40, preferably 4 to 12 and a cycloaliphatic radical containing 5 to 15 carbon atoms (5 to 6 ring carbon atoms) and Y represents OH, COOH or NH$_2$, or in which $R^5$ is a difunctional aromatic radical containing 6 to 24 carbon atoms and preferably 6 to 16 carbon atoms, the two valencies forming an angle of 45° to 180°. The difunctional aromatic radicals may be substituted by 1 to 4 $C_{1-4}$ alkyl, $C_{1-4}$ alkoxy, phenyl, phenoxy, benzyl groups or halogen atoms (preferably chlorine and bromine) and, in addition to phenylene, naphthylene and biphenylene radicals, also include phenylene groups attached by oxygen, sulfur, carbonyl, sulfonyl, $C_{1-4}$ alkylene or alkylidene, cyclohexylene or hexylidene or —O(CH$_2$)$_n$O— with n=1 to 4.

Instead of the aliphatic aminocarboxylic acids, the corresponding lactams may also be used, for example caprolactam instead of ε-aminocaproic acid.

Preferred (cyclo)aliphatic aminocarboxylic acids are ε-aminocaproic acid or caprolactam, ω-aminoundecanoic acid, ω-aminododecanoic acid or lauric lactam, 4-aminocyclohexyl carboxylic acid; preferred aromatic aminocarboxylic acids are 4-aminobenzoic acid or 6-amino-2-naphthoic acid.

ε-Aminocaproic acid or caprolactam, 4-aminobenzoic acid and 6-amino-2-naphthoic acid are particularly preferred.

Preferred amino phenols are, for example, 3-aminophenol, 4-aminophenol, 3-amino-2-methyl phenol, 3-amino-4-methyl phenol, 5-amino-1-naphthol, 6-amino-1-naphthol, 5-amino-2-naphthol, 7-amino-2-naphthol, 8-amino-2-naphthol, 6-amino-2-naphthol and 4'-amino-1-hydroxy-biphenyl; 4-aminophenol, 3-aminophenol and 4'-amino-1-hydroxybiphenyl are particularly preferred.

Preferred substituents $R^3$ of formula (II)—depending on their attachment to the other units—are the substituents (XVII) to (XXIV)

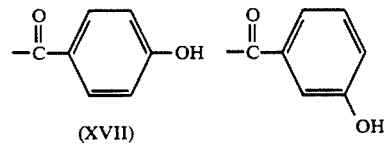

(XVII)                    (XVIII)

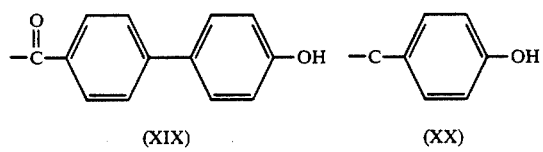

(XIX)                    (XX)

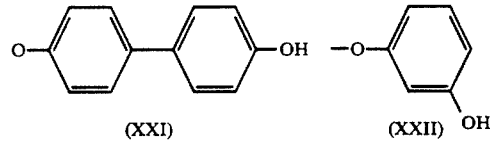

(XXI)                    (XXII)

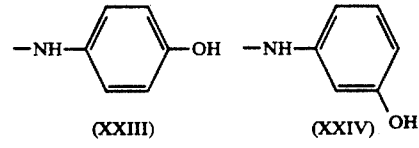

(XXIII)                    (XXIV)

Preferred oligomers corresponding to formula (II) are those which contain on average 3 to 25, preferably 4 to 20 and more preferably 4 to 15 aromatic partial structures, an aromatic partial structure being as defined under formula (I).

The compounds of formula (II) mentioned above are prepared by known melt and transesterification processes which are also used for the production of thermotropic LC polymers (direct esterification process [EP-A 0 088 546], acetate process [EP-A 0 102 719, 134 204], melt transesterification of carboxylic acid phenyl esters with diphenols (diphenyl ester process) [EP-A 072 540, 070 539, 024 499, 45 499, DE-OS 20 25 971, EP 070 539 and EP 132 637]). The chain length is determined by the molar excess of units containing hydroxyl groups over the dicarboxylic acids.

Typical chain terminators, for example monocarboxylic acids or monophenols, may additionally be used.

The compounds of formula (II) according to the invention are prepared in particular by the acetate process and/or the diphenyl ester process. They are oligomeric mixtures with average molecular weights ($\overline{M}n$) of $\leq 4,000$, preferably $\leq 2,500$, which may have both the above-mentioned structural units and also their molecular weight in statistical distribution and show liquid-crystalline properties. They are used as LC additives 2) in the quantities indicated for the production of the new polyamide molding compounds and blends, the liquid-crystalline oligomeric compounds of formula (II) free from aliphatic units being preferred, particularly with statistical distribution of the components in (II).

The low molecular weight, liquid-crystalline additives (II) are used in quantities of 0.1 to 15% by weight, preferably in quantities of 0.3 to 8% by weight and more preferably in quantities of 0.5 to 5% by weight in the production of the polyamide molding compounds according to the invention. They may be used individually or in admixture.

Preferred LC additives 2) are the statistical compounds corresponding to formula (II).

The present invention also relates to the new, liquid-crystalline oligomeric esters and/or ester amides corresponding to formula (II), in which the symbols are as already defined.

The present invention also relates to the use of the polyamide molding compounds according to the invention for the production of moldings, films, fibers, composite materials and other articles and also to the moldings, films, fibers and other articles produced from the new polyamide molding compounds.

Polyamides:

Polyamides 1) suitable for use in accordance with the invention include partially crystalline and amorphous polyamides. They may be used individually or in admixture. Examples of polyamides in the context of the invention are PA 6, 11, 12, 46, 66, 67, 68, 69, 610, 1012, 612, 1010, 1212, 6/66 copolyamides, 6/12 copolyamides, 6/11 copolyamides, 66/11 copolyamides, 66/12 copolyamides, 6/610 copolyamides, 66/610 copolyamides, 6/66/610 terpolyamides, 6I6 copolyamides, 6T,6-, or 6T6 copolyamides, 6IT copolyamides, PA 6I, copolyamides of 1,4-cyclohexane dicarboxylic acid, 2,2,4- and 2,4,4-trimethyl hexamethylene diamine, copolyamides of terephthalic acid, 2,2,4- and 2,4,4-trimethyl hexamethylene diamine, copolyamides of isophthalic acid, lauric lactam and 3,5'-dimethyl-4,4'-diaminodicyclohexyl methane, copolyamides of isophthalic acid, azelaic acid and/or sebacic acid and 4,4'-diaminodicyclohexyl methane (or isomer mixtures), copolyamides of caprolactam, isophthalic acid (+optionally terephthalic acid) and 4,4'-diaminodicyclohexyl methane (or isomer mixtures), copolyamides of caprolactam, isophthalic acid (+optionally terephthalic acid) and isophorone diamine, copolyamides of isophthalic acid (+optionally terephthalic acid) and/or other aromatic or aliphatic dicarboxylic acids, hexamethylene diamine and/or optionally alkyl-substituted hexamethylene diamines and 4,4'-diaminodicyclohexyl amines alkyl-substituted adjacent the amino groups and also other copolyamides or mixtures of different polyamides of components of the type normally used for polyamides. Polyamide block polymers, such as polyether and polyether ester amides, may also be used.

Polyamides obtainable from dicarboxylic acids and diisocyanates are also suitable (for example copolyamides of adipic acid, azelaic acid and 4,4'-diphenylmethane diisocyanate and copolyamides of terephthalic acid, azelaic acid, 4,4'-diphenylmethane diisocyanate and 2,4-(2,6)-tolylene diisocyanate).

Preferred polyamides, which may be used individually or in admixture, are PA 6, 46, 66, 610, 1012, 11, 12, 1212, 616, 61, 6T/6, 6T6, 6/66 copolyamides, copolyamides of caprolactam tam, isophthalic acid and isophorone diamine, copolyamides of isophthalic acid (+optionally terephthalic acid), azelaic acid and 4,4'-diaminodicyclohexyl methane (or isomer mixtures) and copolyamides of isophthalic acid (+optionally terephthalic acid), caprolactam and 4,4'-diaminodicyclohexyl methane (or isomer mixtures).

Polyamide 6 and 66 are particularly preferred.

Blending Components

Suitable polymeric blending components (one of the possible additives according to 3)) for the production of the new free-flowing polyamide blends which, in addition to the polyamides, always contain at least one polymeric blending component include, for example, diene rubbers, acrylate rubbers, polyethylenes, polypropylenes, ethylene/propylene copolymers, ethylene/1-butene copolymers, ethylene/propylene/diene terpolymers, ethylene and/or propylene/acrylic acid/acrylate copolymers, ethylene/vinyl acetate copolymers, polyoctenylenes, polystyrenes, (α-methyl)styrene/(meth)acrylonitrile copolymers,(meth)-acrylonitrile/butadienes/(α-methyl) styrene polymers (ABS), high-impact polystyrenes, polycarbonates, aromatic polyester (carbonates), polyesters such as, for example, polyethylene terephthalate, polysulfones, polyphenylene oxides, polyether ketones, polyarylene sulfides, polyether ether ketones, polyamide imides, polyether sulfones, polyether imides, polyester imides and polyimides of the type known from the prior art as blending components or modifiers. These blending components may be used individually or in admixture with one another.

The polymeric blending components should be—optionally at least partly—chemically modified in such a way that the two phases are partly coupled, for example through carboxylic acid groups. This may be done, for example, by using a copolymer of ethylene and/or propylene and small quantities of acrylic acid or an ethylene/propylene/diene polymer grafted with small quantities of maleic anhydride or a polyphenylene oxide grafted with small quantities of maleic anhydride either individually or in admixture with unmodified blending components. The two phases may also be coupled through ester or epoxide groups. They may also be coupled, for example, through the presence of suitable low molecular weight or polymeric compatibility promoters; for example, an acrylonitrile/styrene/acrylic acid terpolymer may be used as compatibility promoter in blends with ABS. The blending components may also contain reactive terminal groups which are capable of reacting with the polyamide, for example amino- or carboxyl-terminated polydiene rubbers.

The rubbers may also be grafted in a core/shell structure.

According to the invention, it is also possible to obtain mixtures of polyamides with more than one polymer or blending component, for example blends of polyamide 66, polyphenylene oxide and high-impact polystyrene or blends of polyamide 66, aromatic polyesters and an impact modifier. In mixtures such as these, the polyamide content should be no less than 30% by weight and preferably no less than 50% by weight, based on the final mixture.

The polymeric blending components may also be mixed in advance (premixed) with polyamides or mixtures of polyamides to form polyamide blends or are preferably used as one of the additives according to 3). In this case, at least one polyamide, at least one polymeric blending component, at least one LC additive 2) corresponding to formula (I) and/or (II) and, optionally, other standard additives 3), such as glass fibers or even stabilizers, are mixed in the melt (preferably in extruders).

In the case of polyamide blends, therefore, at least one additive 3), namely the polymeric blending component, is always present in the final polyamide blend in addition to polyamides 1) and the LC flow promoters 2).

The present invention also relates to the use of the liquid-crystalline, low molecular weight esters and/or ester amides (I) and/or the oligomeric esters and/or ester amides (II) as LC flow promoter 2) in quantities of 0.1 to 15% by weight (or in the preferred quantities mentioned above) in the production of polyamide molding compounds. The present invention also relates to a process for the production of the new free-flowing polyamide molding compounds by mixing of at least one polyamide 1), at least one LC flow promoter (I) and/or (II) 2) and optionally the additives 3) in the melt; the additives 3) may even have been introduced into the polyamide 1) beforehand in a separate step, so that a correspondingly modified polyamide 1) is used. The new polyamide molding compounds are preferably produced in extruders or kneaders.

The addition of liquid-crystalline polymers to thermoplastics is known (cf. for example EP-OS 0 030 417). In general, however, the limited compatibility of the thermoplastics with the liquid-crystalline polymers is a disadvantage.

Infusible, whisker-like poly-(p-hydroxybenzoate) crystals are described as a reinforcing component in U.S. Pat. No. 4,673,724. On account of their very high melting or softening points, however, these crystals are very difficult to produce and are particularly incompatible with other polymers.

Mixtures of liquid-crystalline polymers and amorphous thermoplastics produced in situ are also known (cf. for example G. Kiss, Polymer Engineering & Science, 27, pages 410–423 (1987). However, mixtures such as these have the disadvantage that the reinforcing effects obtainable depend to a large extent on the mixing conditions and reproducible processing conditions are often difficult to establish.

In addition, in the production of composites of the type in question, the mixing components have very different melt viscosities under processing conditions, so that only a limited number of suitable polymers is available for the production of such composites.

Chemically reactive, liquid-crystalline aromatic esters which condense into the polymer chain by transesterification at relatively high temperatures are described in U.S. Pat. No. 4,650,836 as processing aids for conventional thermoplastics, such as aromatic polyesters, or for liquid-crystalline polymers which are very difficult to process by the methods normally used for thermoplastics. However, the thermoplastics are chemically changed as a result of the incorporation of the aromatic liquid-crystalline esters in the polymer chain. The disadvantage of this is that different incorporation ratios and, hence, non-reproducible properties are obtained in dependence upon the processing conditions. However, the surprising effect of the mixture according to the invention is not present in copolymers of this type.

The free-flowing molding compounds according to the invention may be produced by any of the methods normally used for mixing in the processing of thermoplastics under such conditions (residence times/temperatures) that very little, if any, transesterification takes place and the liquid-crystalline additives are substantially unreacted.

To produce the free-flowing polyamide molding compounds according to the invention containing LC flow promoters 2), the polyamide component(s) 1), the LC flow promoters (I) and/or (II) 2) and the additives 3) optionally used (for example blending components, reinforcing materials, stabilizers, etc.) may be mixed together in the melt. The polyamide molding compounds according to the invention are preferably produced by mixing all the starting components in standard screw extruders. The liquid-crystalline LC flow promoter 2) may be introduced into the extruder with the polyamide component 1) at the outset or may be added to the melts to be extruded at a later stage during the extrusion process.

The LC flow promoters (I) and/or (II) 2) may therefore be introduced at any time during the production of the molding compounds according to the invention. They may also be added immediately before the polyamide molding compounds are processed. The LC additives 2) may be added as such or even in the form of concentrates in a (preferably relatively low-melting) polymer.

The polyamides 1) may contain the additives 3) already incorporated. However, the additives 3) are preferably mixed together with the liquid-crystalline components 2) and the polyamides 1) in a single operation.

The free-flowing PA molding compounds modified with LC flow promoters 2) in accordance with the invention may contain other standard additives 3) in quantities of from 0.001 to 150% by weight and preferably in quantities of 0.01 to 100% by weight, based on the total weights of 1) and 2). Other standard additives suitable for use in accordance with the invention are reinforcing materials (glass fibers, aramide fibers, carbon fibers, glass beads, $SiO_2$, chalk, talcum, kaolin, mica, etc.), plasticizers, antioxidants, pigments, dyes, weathering stabilizers (or stabilizer combinations), lubricants, flow aids, mold release agents, nucleating agents, such as polyarylene sulfides for example, additives which reduce the uptake of water (for example monophenols, bisphenols, (alkyl)phenolformaldehyde condensates etc.), flameproofing agents and other well-known additives of the type which have been proposed for corresponding polyamide materials. The additives 3) independently of one another may be used individually or in the form of a concentrate. However, they may also be completely or partly present in the polyamides 1).

The polyamide molding compounds according to the invention may be processed, for example, by injection molding and extrusion to form moldings and other articles. By virtue of their drastically improved flowability, they are particularly suitable for complicated moldings of large surface area which otherwise would have to be produced with more equipment for processing, often with surface faults, or which in many cases could not even be produced at all.

They are particularly suitable for use in the automotive field.

Even where small quantities of LC additive 2) are used, the PA molding compounds according to the invention are distinguished by a drastically increased flowability and, in some cases, also by improved mechanical properties and heat resistance values. They are also distinguished by reduced water uptake and by a higher crystallization rate and degree of crystallization. Accordingly, they represent a valuable addition to the state of the art.

The invention also relates to the use of additives (I) and (II) according to the invention as additives for other thermoplastics, for example PPS, thermoplastic polyurethanes, ABS, PVC, polysulfones, polyethylene, polypropylene and others.

The following Examples are intended to illustrate the invention without limiting it in any way.

EXAMPLE 1

4-(4-Hydroxybenzoyloxy)-benzoic Acid
4-(4-Hydroxybenzoyloxy)-phenyl Ester

1st stage: 4-hydroxyphenyl-4-hydroxybenzoate 138.1 g p-hydroxybenzoic acid and 110.1 g hydroquinone are suspended with 2 g boric acid and 2.5 g sulfuric acid in 900 ml xylene and the resulting suspension is heated under reflux until the elimination of water is complete. The product is filtered off under suction, dried and washed with dilute Na bicarbonate solution, redried and dissolved in 500 ml acetone. The solution is filtered off hot from undissolved constituents and the product is precipitated from water, filtered under suction and dried. Yield: 182 g, Mp.: 245°–247° C.

2nd stage: 4-(4-carbobenzoxybenzoyloxy)-benzoic acid 4-(4-carbobenzoxybenzoyloxy)-phenyl ester 34.5 g 4-hydroxyphenyl-4-hydroxybenzoate are suspended with 24.9 g pyridine in 300 ml methylene chloride and 35.4 g 4-carbobenzoxybenzoyl chloride are added to the resulting suspension over a period of 3 h at 0° C. After 2 h, the solvent is distilled off in vacuo and the residue is made up with 140 ml 5% hydrochloric acid. The insoluble product was filtered off under suction, washed with water and dried. Yield: 50.3 g (91% of the theoretical) 3rd stage: 4-(4-hydroxybenzoyloxy)-benzoic acid 4-(4-hydroxybenzoyloxy)-phenyl ester The product of stage 2 is suspended in 150 ml ethyl acetate and, after the addition of 0.2 palladium carbon, the suspension is hydrogenated for 2 h under 2 atms. pressure. The catalyst is filtered off and the solvent is distilled off in vacuo.

The colorless solid is generally TLC-pure and, for further purification, may be recrystallized from DMF. Yield: 38 g.

Using a polarization microscope, an LC phase can be detected in the 165°–280° C.

EXAMPLE 2

Statistical LC ester 207.2 g p-hydroxybenzoic acid, 165.2 g hydroquinone, 124.6 g terephthalic acid, 0.08 g magnesium and 306.6 g acetanhydride are weighed into a reaction vessel equipped with a stirrer, column and distillation bridge. Elimination of the acetic acid began at an internal temperature of 160° C. As the distillation rate decreased, the reaction temperature was slowly increased to 250° C.

On completion of distillation, the pressure was reduced to 1 mbar over a period of 30 minutes. During the vacuum phase, residual amounts of acetic acid were eliminated over a period of 2 h.

The product was filled into a tin can and size-reduced after cooling. Yield: 450 g.

Using a polarization microscope, a liquid crystalline phase was detected in the 180°–300° C. range.

EXAMPLE 3

207.2 g p-hydroxybenzoic acid, 165.2 g hydroquinone, 124.6 g isophthalic acid, 0.08 g magnesium and 306.6 g acetanhydride are weighed in and reacted as in Example 2. Yield: 490 g.

Using a polarization microscope, a liquid crystalline phase was detected in the 170°–320° C. range.

EXAMPLE 4

Polyamide 6 granules, relative solution viscosity 2.9 in m-cresol, were compounded with increasing quantities of the additives of Examples 1 and 2 in a single-screw extruder at T=290° C. and the granules were processed to test specimens (80×10×4 mm) which were subjected to the bending test according to DIN 53 452.

Water absorption was also determined (15 days).

The results are shown in Table 1.

The Comparison Example clearly shows the improvement in flow by the LC additives (reduction of melt viscosity).

Further property improvements are the increase in rigidity for high outer fiber strain and the reduction in water absorption.

TABLE 1

(Example 4)
Compounding of a polyamide 6 having a rel. solution viscosity in m-cresol of approx 2.9

| Additive of Example | Conc. [%] | $\eta rel$ | $\eta melt$ T = 270° C. $\tau = 100\,s^{-1}$ | Water absorption [%] | E modulus in bending [MPa] | Flexural strength [MPa] | Outer fiber strain [%] |
|---|---|---|---|---|---|---|---|
| Comparison Example | 0 | 2.85 | 115 | 8.6 | 2698 | 112 | 5.69 |
| 2 | 1 | 2.8 | 100 | 8.4 | 2745 | 112 | 5.87 |
|   | 3 | 2.75 | 90 | 7.5 | 2715 | 112 | 5.82 |
|   | 5 | 2.75 | 40 | 7.2 | 2812 | 114 | 5.88 |
| 1 | 1 | 2.85 | 100 | 8.2 | 2760 | 112 | 5.70 |
|   | 3 | 2.80 | 85 | 7.1 | 2780 | 114 | 5.80 |

TABLE 1-continued (Example 4)
Compounding of a polyamide 6 having a rel. solution viscosity in m-cresol of approx 2.9

| Additive of Example | Conc. [%] | $\eta_{rel}$ | $\eta_{melt}$ T = 270° C. $\tau = 100\ s^{-1}$ | Water absorption [%] | E modulus in bending [MPa] | Flexural strength [MPa] | Outer fiber strain [%] |
|---|---|---|---|---|---|---|---|
| | 5 | 2.75 | 55 | 7.0 | 2850 | 114 | 5.75 |

EXAMPLE 5

Polyamide 6,6 granules, relative solution viscosity 2.9 in m-cresol, were compounded with the additives of Examples 1 and 2 in a single-screw extruder at T=290° C. The granules were processed to test specimens (80×10×4 mm) which were subjected to the bending test according to DIN 53 452.

Water absorption was also determined (15 days).
The results are shown in Table 2.

The Comparison Example demonstrates the improvement in flow (reduction of melt viscosity). Further property improvements are the reduced water absorption and the increase in rigidity for high outer fiber strain.

TABLE 1

(Example 5)
Compounding of a polyamide 6,6 having a rel. solution viscosity in m-cresol of approx 2.9

| Additive of Example | Conc. [%] | $\eta_{rel}$ | $\eta_{melt}$ T = 270° C. $\tau = 100\ s^{-1}$ | Water absorption [%] | E modulus in bending [MPa] | Flexural strength [MPa] | Outer fiber strain [%] |
|---|---|---|---|---|---|---|---|
| Comparison Example | 0 | 2.85 | 200 | 7.65 | 2856 | 118 | 5.83 |
| 1 | 1 | 2.85 | 175 | 7.20 | 2900 | 120 | 6.00 |
| | 3 | 2.85 | 135 | 6.20 | 2940 | 124 | 6.15 |
| | 5 | 2.90 | 80 | 6.0 | 3060 | 124 | 5.80 |
| 1 | 1 | 2.85 | 150 | 7.35 | 2956 | 124 | 6.24 |
| | 3 | 2.80 | 85 | 6.55 | 3063 | 126 | 6.01 |
| | 5 | 2.82 | 40 | 5.80 | 3107 | 115 | 4.21 |

We claim:

1. Free-flowing polyamide molding composition comprising a mixture of
   i) 85 to 99.9% by weight polyamides and
   ii) 0.1 to 15% by weight low molecular weight, liquid-crystalline hydroxyl esters and/or ester amides corresponding to formula (I)

$$R^1\left[\left(\underset{}{\bigcirc}-M^1-\underset{}{\bigcirc}-O-\overset{O}{\underset{\|}{C}}\right)_n\left(Ar-\overset{O}{\underset{\|}{C}}-O\right)_m\right]_o \quad (I)$$

$$\left[\underset{}{\bigcirc}-M^2-\underset{}{\bigcirc}\right]_p R^2$$

in which
—Ar is a $C_{6-20}$ aromatic radical which is mononuclear or polynuclear wherein the polynuclear radical is either attached by a bond or fused, $R^1$ and $R^2$ is the same or different and each represents a group of the formula (III)–(XI)

$$-Y-\underset{}{\bigcirc}-OH \quad (III)$$

$$-Y-\underset{OH}{\bigcirc} \quad (IV)$$

$$-Y-\underset{OH}{\bigcirc} \quad (V)$$

(VI)

$$-X\overset{O}{\underset{\|}{C}}-\underset{}{\bigcirc}-OH \quad (VII)$$

$$-X\overset{O}{\underset{\|}{C}}-\underset{OH}{\bigcirc} \quad (VIII)$$

$$-X\overset{O}{\underset{\|}{C}}-\underset{OH}{\bigcirc} \quad (IX)$$

$$-\overset{O}{\underset{\|}{C}}-X-\underset{}{\bigcirc}-OH \quad (X)$$

$$-\overset{O}{\underset{\|}{C}}-X-\underset{OH}{\bigcirc}$$

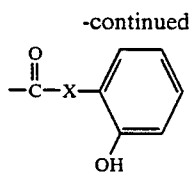

10 wherein

Y is a chemical bond, a difunctional $C_{1-10}$ hydrocarbon radical or an $-SO_2$ group;

X is O or NH; and wherein the aromatic rings in formulae (III)-(XI) are unsubstituted or substituted by halogen atoms or alkyl groups;

$-M^1$ and $-M^2$ are the same or different and each represents radicals with two bonds corresponding to formula I.1) to I.11)

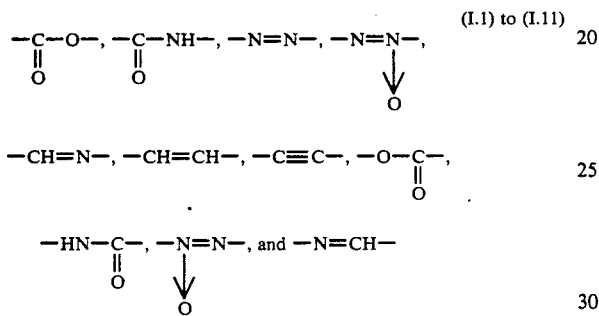

m is 0, 1 or 2,
n is 1 or 2,
o is 1, 2, 3 or 4 and
p is 0 or 1,
and/or liquid-crystalline oligomeric easters and/or easter amides corresponding to formula (II) with statistical distribution of the structural units

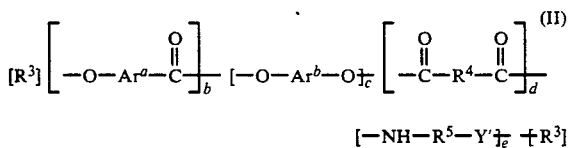

in which $Ar^a$ is a difunctional, unsubstituted or substituted mononuclear or polynuclear aromatic radical containing 6 to 24 carbon atoms which polynuclear radical is directly bonded or even fused;

$Ar^b$ is a difunctional, unsubstituted or substituted, mononuclear or polynuclear aromatic radical containing 6 to 30 carbon atoms;

$R^4$ and $R^5$ represent alkyl wherein $R^4$ contains 0 to 40 carbon atoms and $R^5$ contains 3 to 40 carbon atoms or both $R^4$ and $R^5$ together represent a cycloaliphatic radical containing 5 to 15 carbon atoms or an unsubstituted, difunctional, mononuclear or polynuclear aromatic radical containing 6 to 24 carbon atoms;

Y' represents —O—,

or —NH—,
b is 0 to 10;
c is 1 to 9;
d is 0 to 9;
e is 0 to 3
and in which $R_3$, depending on its attachment to the other units, represents substituents corresponding to formulae (XII)-(XIV)

where the symbols are as defined above and wherein the average molecular Mn of the units corresponding to formula (II) being no greater than 4,000 and, optionally, iii) from 0.001 to 150% by weight, based ion the total weight of components i) and ii), of conventional additives.

2. Free-flowing polyamide molding composition claimed in claim 1 wherein the amount of ii) is 0.3 to 8% by weight.

3. Free-flowing polyamide molding composition claimed in claim 1 wherein the amount of ii) is 0.5 to 5% by weight.

4. Free-flowing polyamide molding composition claimed in claim 1 wherein Y in formulae (III) to (V) is a chemical bond or $-C(CH_3)_2-$.

5. Free-flowing polyamide molding composition claimed in claim 1 wherein for formula (II), b is 0 to 8, c is 1 to 7, d is 0 to 7 and e is 0 to 2.

6. Free-flowing polyamide molding composition claimed in claim 1 wherein for formula (II), b is 0 to 4, c is 1 to 4, d is 0 to 3 and e is 0 to 2.

7. Free-flowing polyamide molding composition claimed in claim 1 wherein the average molecular weight of the compound corresponding to formula (II) is no greater than 2,500.

8. Free-flowing polyamide molding compositions claimed in claim 1 wherein the units of the liquid-crystalline compounds corresponding to formula (II) comprise members selected from the group consisting of 4-hydroxy-3-methylbenzoic acid, 4-hydroxy-3-methoxybenzoic acid, 4-hydroxybenzoic acid, 3-hydroxybenzoic acid, 6-hydroxy-2-naphthoic acid, hydroquinone, 4,4'-dihydroxydiphenyl, 4,4'-dihydroxydiphenyl ether, 4,4'-dihydroxydiphenyl ethane, 4,4'-dihydroxydiphenoxy ethane, 3,5'dihydroxydiphenyl, 3,5'-dihydroxydiphenyl ether, 1,5-dihydroxynaphthalene, 2,6-dihydroxynaphthalene, 1,4-dihydroxynaphthalene, methyl hydroquinone, phenyl hydroquinone, 2,2'-dimethyl-4,4'-dihydroxydiphenyl, 3,3',5,5'-tetramethyl-4,4'-dihydroxydiphenyl, 1,2-(2-chloro-4-hydroxyphenoxy)-ethane, 4-methoxy-2,6-dihydroxynaphthalene, resorcinol, 3,4'-dihydroxydiphenyl, 1,6-dihydroxynaphthalene, 1,7-dihydroxynaphthalene, 2,7-dihydroxynaphthalene, 4-chlororesorcinol, 4-phenylresorcinol, 4-ethoxyresorcinol, 2,5-dichloro-1,6-dihydroxynaphthalene, 4-methoxy-2,7-dihydroxynaphthalene, 1,4-naphthalenedicarboxylic acid, 1,5-naphthalenedicarboxylic acid, 2,6-naphthalenedicarboxylic acid, biphenyl-4,4'-dicarboxylic acid, biphenyl-3,3'-dicarboxylic acid, diphenoxyethane-4,4'-dicarboxylic acid, diphenylether- 4,4'-dicarboxylic acid, methyltrephthalic acid, methoxyterephthalic acid, chloroterephthalic acid, 4-chloronaphthalene-2,7-dicarboxylic acid, 2,6-naphthalenedicarboxylic acid, 2,7-naphthalenedicarboxylic acid, biphenyl-3,4'-dicarboxylic acid, 4-methylisophthalic acid, 5-methylisophthalic acid, diphenylether-4,4'-dichloro-3,'-dicarboxylic acid, isophthalic acid, terephthalic acid, ε-aminocaproic acid, caprolactam, ω-aminoundecanoic acid, ω-aminododecanoic acid, lauric lactam, 4-aminocyclohexyl carboxylic acid, 4-aminobenzoic acid, 6-amino-2-naphthoic acid, 3-aminophenol, 4-aminophenol, 3-amino-2-methyl phenol, 3-amino-4-methyl phenol, 5-amino-1-naphthol, 6-amino-1-naphthol, 5-amino-2-naphthol, 4'-amino-1-hydroxybiphenyl, oxalic acid, succinic acid, adipic acid, suberic acid, azelaic acid, trimethyl adipic acid, sebacic acid, dodecanedioic acid, dimer fatty acids, 1,4-cyclohexanedicarboxylic acid, benzoic acid, 4-methylbenzoic acid, 4-methoxybenzoic acid and 4-biphenyl carboxylic acid.

9. Free-flowing polyamide molding composition claimed in claim 1 wherein the compound corresponding to formula (II) has on average 3 to 25 aromatic partial structures.

10. Free-flowing polyamide molding composition claimed in claim 1 wherein the compound corresponding to formula (II) has on average 4 to 20 aromatic partial structures.

11. Free-flowing polyamide molding composition claimed in claim 1 wherein i) is polyamide 6, 66, 46, 610, 11, 12, 1012, 1212, 6I6, 6I, 6T/6I, 6T6, 6/66 copolyamides, copolyamides of caprolactam, isophthalic acid, azelaic acid and 4, 4'-diaminodicyclohexyl methane, thereof.

12. Free-flowing polyamide molding composition claimed in claim 1 wherein i) is polyamide 6 or polyamide 66.

13. Polyamide molding composition claimed in claim 1 wherein iii) comprises diene rubbers, acrylate rubbers, polyethylene, polypropylene, ethylene/propylene copolymers, ethylene/1-butene copolymers, ethylene/propylene/diene terpolymers, ethylene/acrylic copolymers, propylene/acrylic copolymers, ethylene/vinyl acetate copolymers, polyoctenylenes, polystyrenes, styrene/(meth)acrylonitrile copolymers, (meth)acrylonitrile/butadiene/styrene polymers (ABS), high-impact polystyrenes, polycarbonates, aromatic polyester (carbonates), polyesters, polysulfones, polyphenylene oxides, polyether ether ketones, polyether imides, polyester imides, polyamide imides or polyimides as polymeric blending components.

14. Free-flowing polyamide molding composition claimed in claim 1 wherein iii) comprises glass fibers, aramide fibers, carbon fibers, glass beads, $SiO_2$, chalk, $TiO_2$, talcum, kaolin, mica or $TiO_2$ as reinforcing materials, plasticizers, antioxidants, pigments, dyes, weathering stabilizers, lubricants, flow aids, mold release agents, nucleating agents, additives which reduce water uptake flameproofing agents or polymeric blending components.

15. A process for the production of the free-flowing polyamide molding composition claimed in claim 1 which comprises melt mixing and compounding components i), ii) and iii) in an extruder.

16. Articles of manufacture comprising moldings, films, fibers and composite materials containing the molding composition claimed in claim 1.

* * * * *